United States Patent [19]

Chiu

[11] Patent Number: 5,327,886
[45] Date of Patent: Jul. 12, 1994

[54] ELECTRONIC MASSAGE DEVICE WITH COLD/HOT COMPRESS FUNCTION

[76] Inventor: Cheng-pang Chiu, 4th Fl., No. 11, 199 Lane, Section 4, Ren-ay Road, Taipei, Taiwan

[21] Appl. No.: 931,373

[22] Filed: Aug. 18, 1992

[51] Int. Cl.⁵ ............................................... A61F 7/00
[52] U.S. Cl. ...................................... 607/96; 601/70; 601/15
[58] Field of Search .................. 128/24.1, 24.2, 24.3, 128/24.4, 24.5, 67, 399, 402, 32, 36

[56] References Cited

U.S. PATENT DOCUMENTS

| | | | |
|---|---|---|---|
| 2,687,718 | 8/1950 | Britton | 128/36 |
| 3,207,159 | 11/1962 | Tateisi | 128/399 |
| 3,710,784 | 1/1973 | Taylor | 128/24.2 |
| 3,736,920 | 6/1973 | Mathers | 128/57 |
| 4,640,284 | 2/1987 | Ruderian | 128/399 |
| 4,887,594 | 12/1989 | Siegel | 128/36 |
| 5,097,828 | 3/1992 | Deutsch | 128/399 |
| 5,117,815 | 6/1992 | Gentry | 128/36 |

*Primary Examiner*—Robert A. Hafer
*Assistant Examiner*—David J. Kenealy

[57] ABSTRACT

An electronic massage device with cold/hot compress function includes an eccentric wheel driven by a motor to rotate and thereby generates vibration, a thermoelectric module used to provide the cold or heat source needed by the cold or hot compress, respectively, a cooling fan used to exhaust extra hot air generated during cold compress, and a set of thermoswitches used to control the hot compress temperature. The massage device may be used to soothe general body impairments through sports by cold compress alone or by hot compress together with massage.

1 Claim, 5 Drawing Sheets

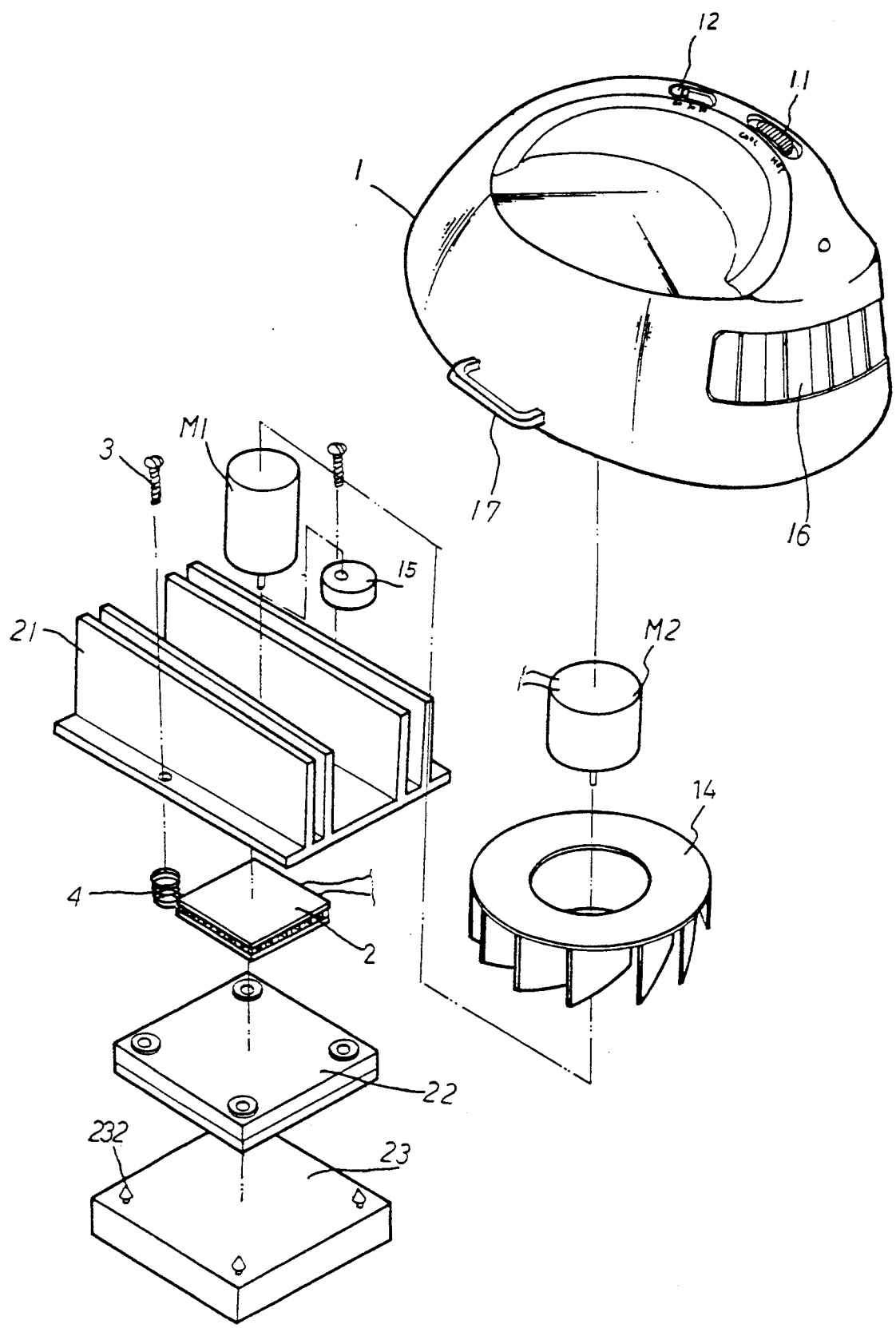
F I G. 1

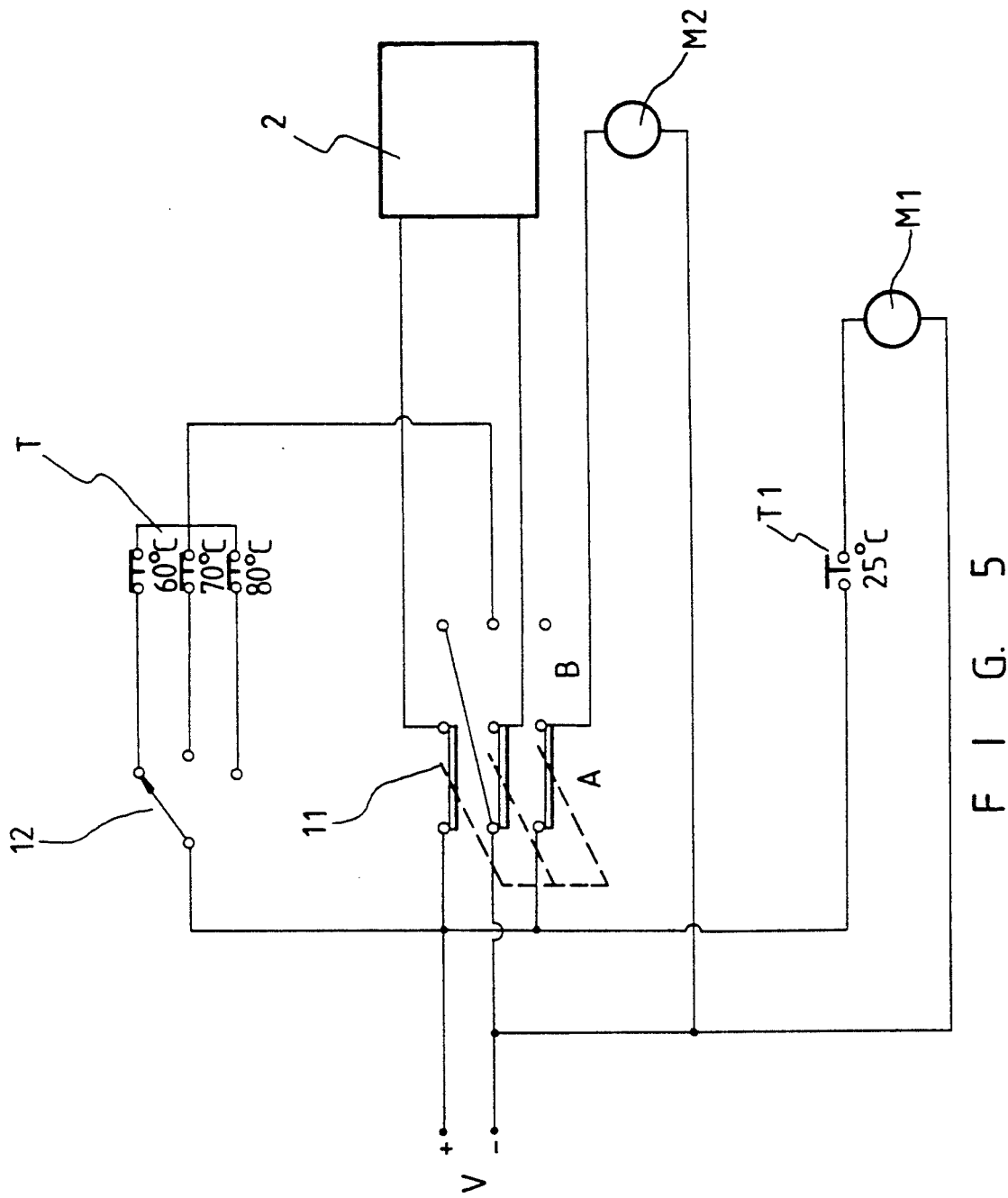

ELECTRONIC MASSAGE DEVICE WITH COLD/HOT COMPRESS FUNCTION

BACKGROUND OF THE INVENTION

The present invention relates to an electronic massage device which has the function of cold/hot compress in addition to the basic massage performance.

Conventional massage devices that are commercially available are used to massage without any cold/hot compress effect. Means such as ice-bags for cold compress or hot water bags, infra-red for hot compress and other medical equipments for such purposes are either not practical or inconvenient in use. Following the upgraded living quality nowadays, various kinds of healthful sports are more and more popular in people of all ages and of all ranks. However, different degree of body impairments through sports increase, too. Therefore, it is desirable to have a device which is not only convenient and practical in use but also capable of providing the functions of massage, cold compress, and hot compress that are most helpful in soothing sports impairments.

SUMMARY OF THE INVENTION

A high-tech electronic element, namely, thermoelectric module, is therefore utilized to develop the electronic massage device of the present invention which combines the function of cold/hot compress with massage in one single unit. One of the properties of the thermoelectric module is that it can be used as a cold or heat source just by switching the flow direction of current passing through it. When such cold/heat source is transferred to the user's body through silicon rubber, a kind of heat conduction material giving soft and comfortable feeling when touching it, plus a massage effect provided by a vibration mechanism incorporated in the present invention, cold compress alone, massage alone, or massage together with hot compress can be provided by one single unit as selected. Such device is practical and convenient in use, easy in operation, and eliminates the drawbacks existed either in the conventional massage devices or in the common cold/hot compress means.

A further object of the present invention is to provide the above massage device in which a set of parallel thermal switches with different induction temperatures is incorporated in the circuit. Users may select preferred hot compress temperature by controlling a temperature selection switch.

A still further object of the present invention is to provide the above massage device in which a cooling fan is incorporated to exhaust extra heat from the device to lower the temperature inside the unit when it is used for cold compress.

BRIEF DESCRIPTION OF THE DRAWINGS

The features, functions, and operation of the present invention may be best understood by referring to the following detailed description of the preferred embodiments and the accompanying drawings wherein FIG. 1 is a three-dimensional analytical perspective of the present invention;

FIG. 5 is a circuit diagram of the present invention.

DETAILED DESCRIPTION OF THE PREFERRED EMBODIMENTS

Figure 2:
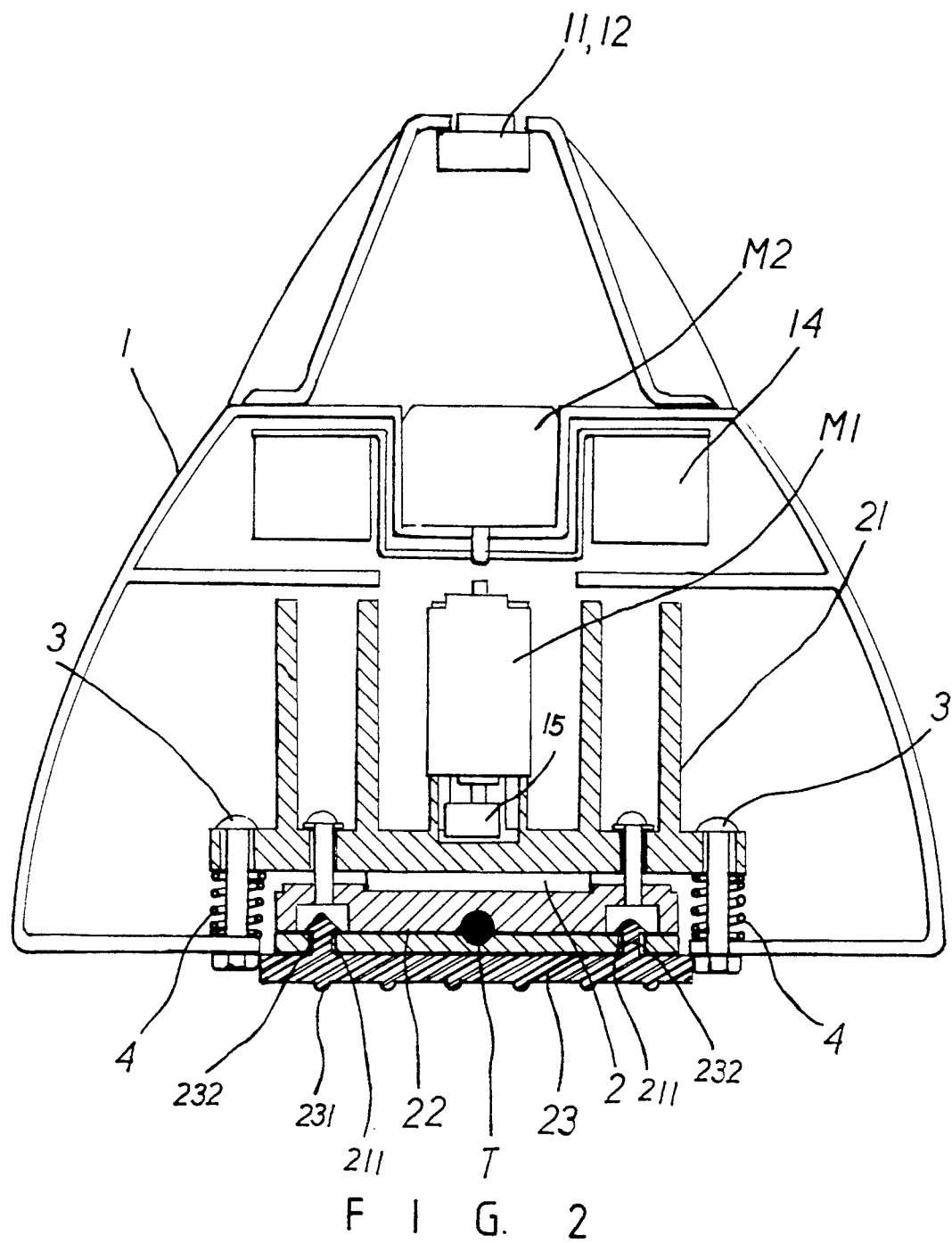
FIG. 2 is a vertical, sectional view of the present invention.

Please refer to FIG. 1, the present invention includes a housing 1 inside it a thermoelectric module 2, a first motor M1, a second motor M2, a cooling fan 14, an eccentric wheel 15, an upper radiating fin 21, and a lower radiating fin 22 are disposed, and a silicon rubber bottom pad 23. On top of the housing 1, a first switch 11 and a second switch 12 are provided. The first switch 11 is a three-pole double-throw switch for controlling the current passing the thermoelectric module 2 to be a positive or a reverse current so that the thermoelectric module 2 may generate cooling effect (for cold compress) or thermal effect (for hot compress), respectively. The second switch 12 is a temperature selection s witch, it induces the hot compress temperature through a set of parallel thermoswitches T (provided within the lower radiating fin 22 for detecting the hot compress temperature) and thereby controls the electrical connection of the thermoelectric module 2, and the temperature desired, accordingly. The first motor M1 is fixed on and within the upper radiating fin 21 for driving the eccentric wheel 15 connected thereto to rotate and generate vibration effect. The second motor M2 is used to drive the cooling fan 14 so that extra hot air produced during cold compress and filled in the housing 1 can be stirred by the cooling fan 14 and thereby exhausted from the housing 1 via a cooling grid 16. The exhaustion of extra hot air out of the housing 1 may cool the device and thereby lower the cold compress temperature.

Please refer to FIG. 2 now. The thermoelectric module 2 is disposed between the upper radiating fin 21 and the lower radiating fin 22. When the thermoelectric module 2 is electrically connected, a temperature difference of about 60° C. would exist between its two outer surfaces (the temperature of lower surface will be higher than that of upper surface, if the device is selected for hot compress, and lower if for cold compress). When the flow direction of current passing the thermoelectric module 2 is reversed, the temperature difference effect appears on two outer surface is reversely changed. The upper radiating fin 21 is supported on the inwardly and laterally extended bottom periphery of the housing 1 by two springs 4 separately disposed on a side flange of the upper radiating fin 21, and two screws 3 are separately put through the springs 4 and holes formed on the side flanges to fixedly hold the upper radiating fin 21 onto the bottom periphery of the housing 1 so that the upper radiating fin 21 together with the first motor M1 mounted thereon are in a suspension state which tends to enhance the vibration effect produced when the eccentric wheel 15 is driven to rotate.

The lower radiating fin 22 is screwed to the upper radiating fin 21 by screws at adequate positions and has four holes 211 formed at its four corners for receiving protuberances 232 correspondingly provided on upper surface of the silicon rubber pad 23 so that the silicon rubber pad 23 may be easily and detachably assembled to complete the massage device of the present invention. Silicon rubber pads 23 with different bottom protuberance 231 designs may be freely replaced to produce different massage effect. FIG. 5 is a circuit diagram showing the circuit used by the present invention, from which the manner in which the present invention is operated can be clearly seen. The first switch 11 is used to control the flow direction of current passing the thermoelectric module 2. When the lower radiating fin 22 generates cooling effect, that is, the first switch 11 is at a position as indicated by the reference letter A, the second motor M2 is on and starts to operate, that means, heat energy transferred to the upper radiating fin 21 is allowed to be sent out of the housing 1 by means of the operation of the second motor M2. At the same time, the first motor M1 is off without any movement when it senses a lower radiating fin 22 temperature lower than a preset temperature of 25° C. (the first motor M1 is controlled by a first thermoswitch T1 which is a normally open switch and it will turn on the first motor M1 only when the temperature becomes higher than 25° C.). At this time, no vibration, that is, no massage function shall be performed (in medical theraphy, any massage is not allowed during cold compress). However, when the lower radiating fin 22 generates heat effect, that is, the current passing the thermoelectric module 2 is a reverse current and the first switch 11 switches to a position as indicated by the reference letter B, the second motor M2 is off, that means, the upper radiating fin 21 is in low temperature state and there is not any extra heat to be sent out. On the other hand, the first motor M1 senses a temperature higher than the preset temperature and is on to generate vibration, providing the hot compress and massage functions at the same time. Due to the reverse current passing the thermoelectric module 2, the lower radiating fin 22 shall become hot from cold, when its temperature raises to the critical temperature pre-selected for the thermoswitch T1, the thermoswitch T1 will automatically disconnect the circuit and prevents the thermoelectric module 2 from overheating so that the pre-selected temperature can be maintained.

In brief, a user may use the first switch 11 to select the cold or hot compress function, and the second switch 12 to select the working temperature so that the hot compress temperature may be duely adjusted. The operation of the massage device of the present invention is easy and convenient.

Figure 3:
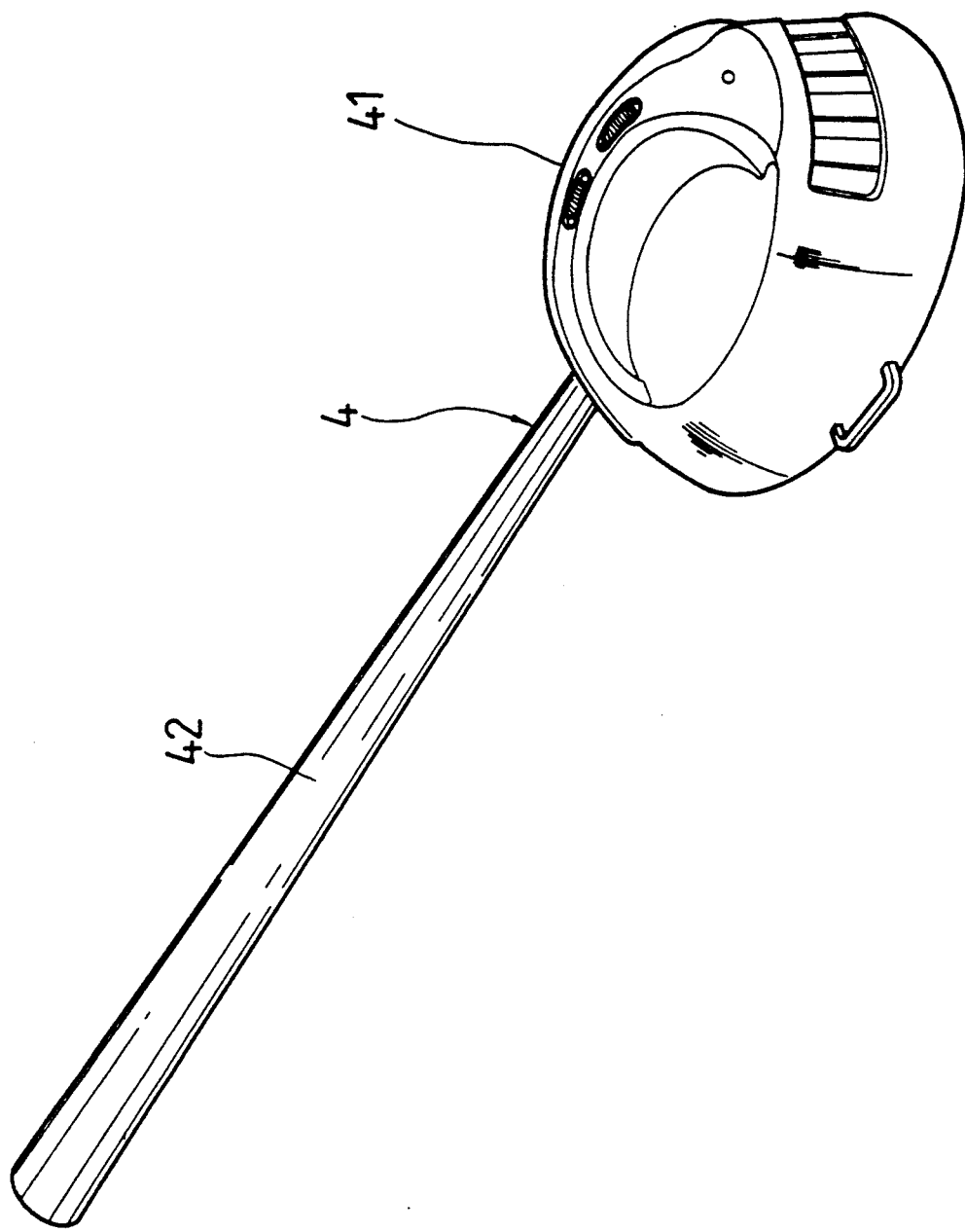
FIG. 3 illustrates an embodiment of the present invention in which an extended handle is attached to the massage device.

FIG. 3 illustrates another embodiment of the present invention in which an extension means 6 (as shown by dotted line in the figure) having an extended handle 62 may be attached to the top of housing 1 by engaging its engaging portion 61 with the housing 1 so that the massage device may be used to massage the user's back.

Figure 4:
FIG. 4 illustrates another embodiment of the present invention in which a belt is fastened to the massage device for conveniently tying the device to the area of body needing massage or cold/hot compress.

The housing 1 may be further provided with two fastening means 17 at its two opposite sides so that a belt 5 can be used together with the fastening means 17 to conveniently tie the massage device to the desired part of the body as shown in FIG. 4, with the bottom protuberances 231 of the silicon rubber pad 23 facing the skin to be massaged.

What is claimed is:

1. An electronic massage device with cold/hot compress function comprising:
    a housing;
    a first motor disposed in said housing;
    an eccentric wheel coupled to said first motor and driven by said first motor in order to generate vibrations;
    a second motor disposed in said housing and disposed above said first motor;
    an electric fan coupled to said second motor and driven by said second motor in order to exhaust heat generated within said housing;
    an upper radiating fin disposed in said housing and located below said first motor and loosely coupled to said housing by at least two bolts;
    means disposed between said upper radiating fin and said housing for resiliently biasing said upper radiating fin away from said housing;
    a lower radiating fin fixed to said upper radiating fin;
    a silicon rubber pad coupled to said lower radiating fin for contacting the users using said electronic massage device, said silicon rubber pad including a bottom surface having a plurality of protuberances formed thereon for contacting and for massaging said users;
    a thermoelectric module disposed between said upper radiating fin and said lower radiating fin and having an upper surface and a lower surface closely contacted with said upper radiating fin and said lower radiating fin, said thermoelectric module generating either lower temperature or high temperature in order to transfer said lower temperature or high temperature to said lower radiating fin and then transfer to said users in order to cool or to heat said users; and
    a switch means disposed in said housing for switching and controlling current direction supplied into said thermoelectric module so as to control said thermoelectric module to generate either lower temperature or high temperature;
    whereby, said users are massaged by said vibrations generated by said eccentric wheel and transmitted to said silicon rubber pad, and said users are cooled or heated by said lower temperature of said high temperature generated by said thermoelectric module.

* * * * *